United States Patent [19]
Jing

[11] Patent Number: 5,500,535
[45] Date of Patent: Mar. 19, 1996

[54] STRESS CELL FOR A SCANNING PROBE MICROSCOPE

[75] Inventor: Tianwei Jing, Tempe, Ariz.

[73] Assignee: Molecular Imaging Corporation, Tempe, Ariz.

[21] Appl. No.: 399,969

[22] Filed: Mar. 7, 1995

[51] Int. Cl.⁶ ..................................... H01J 37/20
[52] U.S. Cl. ...................... 250/440.11; 250/306; 73/105; 73/817
[58] Field of Search ............... 250/440.11, 306; 73/105, 788, 817

[56] References Cited

U.S. PATENT DOCUMENTS

| | | | |
|---|---|---|---|
| 3,759,082 | 9/1973 | Provenzano et al. | 73/817 |
| 5,103,095 | 4/1992 | Elings et al. | 250/440.11 |

FOREIGN PATENT DOCUMENTS 3-221801  9/1991  Japan ........................ 250/306

*Primary Examiner*—Jack Berman
*Attorney, Agent, or Firm*—D'Alessandro & Ritchie

[57] ABSTRACT

A novel stress cell for applying stress in-situ to a sample in a scanning probe microscope. It has a loading clamp mounted on a sample stage which is magnetically mounted to a scanning tunneling microscope or atomic force microscope. A wedge is placed on top of the sample stage. A clamp holds a sample with its two arms pulling the sample against the wedge. It is fastened by a micrometer which is driven by a motor. A force-sensor is placed between the clamp and the stage to measure the force applied. This cell provides a superior stability and straightforward operation procedure for studying stress related problems in materials.

9 Claims, 2 Drawing Sheets

STRESS CELL FOR A SCANNING PROBE MICROSCOPE

BACKGROUND OF THE INVENTION

1. Field of the Invention

This invention relates to a stress cell for a scanning probe microscope (SPM) and its use for studying stress-related problems in material science research. More particularly, it relates to a sample stage which can be attached magnetically or otherwise to a scanning probe microscope, a stressing device mounted on the stage which has a loading clamp with arms that engage two slots on the stage and a force-sensor mounted near the center on the bottom of the stage. A wedge is placed on the sample stage between two clamp-arms. The clamps grip a sample by its edges, pulling it against the wedge. A motor-driven micrometer is fastened to the clamp, and pulls down on the sample to bend it against the wedge, providing a stressed sample the surface of which may then be imaged by conventional scanning probe microscopy techniques including atomic force microscopy and scanning tunneling microscopy.

2. The Prior Art

Problems related to the failure of materials under stress are important in the semiconductor and aerospace industries. For example, stress-induced dislocations and micro cracking cause failure in semiconductor integrated circuits and high strength materials. Various techniques are used for studying these problems. At the high resolution end for in-situ studies, stress related problems like microcracking, lattice structural changes and dislocation propagation under stress are studied by scanning electron microscopy (SEM) and transmission electron microscopy (TEM). In the prior art, stress is often induced by generating a thermal gradient across the sample and examining the structural changes in the sample using SEM or TEM. Light optical microscopy and position sensitive photodetectors have also been used in some cases. These methods often require a high vacuum system because oxidation of the sample at high temperature and corrosion assisted cracking are enhanced by the methods used to induce stress. Although these methods can be used to study thermal stresses, they are not suitable for studying pure mechanical stress (such as film-edge induced stress, strain and misfit dislocations in doped lattices and heteroepitaxy, and stress problems of embedded structural elements). This is because of the temperature dependence of the material properties. A micromanipulator has been used to stretch a sample to generate stress while the sample was examined with optical microscopy, SEM or measurements of its electrical properties.

Optical microscopy is convenient but lacks high resolution. SEM has high resolution (better than 50 nm), but it also has high setup and equipment cost and must be performed in a vacuum. TEM has even better resolution than SEM but it requires a complex sample preparation procedure, a very thin sample and much more expensive equipment. The scanning tunneling microscope (STM) and atomic force microscope (AFM) have proved to be very powerful tools for surface science, being capable of atomic resolution even without the sample in an ultrahigh vacuum. However, the SPM has not as yet been applied to the study of stress related problems due to a lack of stability in the devices available to apply stress to a sample.

OBJECTS AND ADVANTAGES OF THE INVENTION

It is an object of the present invention to provide a stress cell for SPM systems which is easy to use in the typical laboratory by the typical laboratory worker.

It is another object of the present invention to provide a device which can apply stress to a sample with great mechanical stability while the sample is imaged under a scanning probe microscope.

It is still another object of the present invention to produce a stress cell in which a force sensor is incorporated in order to measure the shear modulus of the sample directly.

It is yet another object of the present invention to provide a system which is easy to calibrate and in which the bending angle of the sample can be controlled precisely with a controlled movements of a motor.

These and many other objects and advantages of the present invention will become apparent to those of ordinary skill in the art from a consideration of the drawings and ensuing description of the invention.

SUMMARY OF THE INVENTION

The present invention is directed to a mechanism for stressing a sample to be imaged with a scanning probe microscope. In its simplest embodiment, the stress cell comprises a sample stage, a clamp to hold the sample to be stressed against the sample stage, a stress inducing element, and a drive mechanism to force the sample against the stress inducing element.

According to another aspect of the present invention, a force or stress sensing sensor is included to provide a signal indicative of the level of stress imparted to the sample.

According to another aspect of the present invention, a motor drive may be incorporated into the drive mechanism in order to automate the application of stress.

DESCRIPTION OF THE PREFERRED EMBODIMENTS

Those of ordinary skill in the art will realize that the following description of the present invention is illustrative only and is not intended to be in any way limiting. Other embodiments of the invention will readily suggest themselves to such skilled persons from an examination of the within disclosure.

Figure 1:
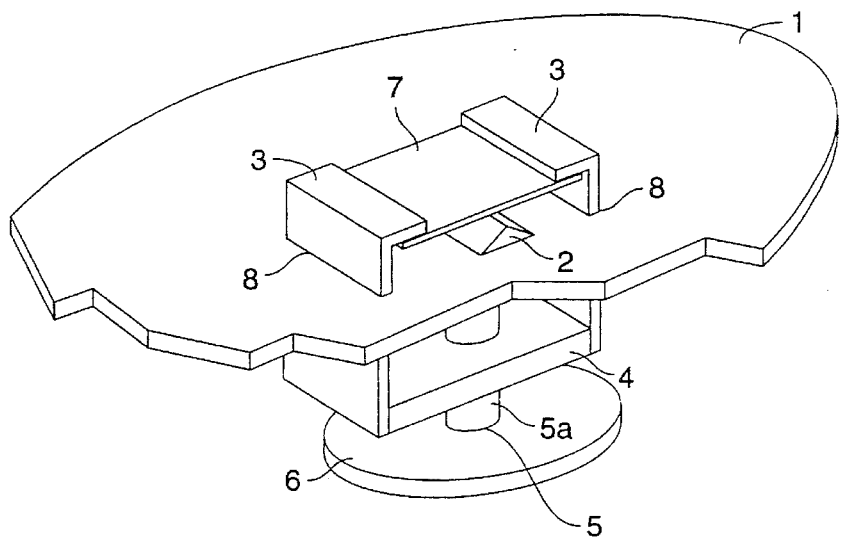
FIG. 1 is a perspective view of a stress cell according to a presently preferred embodiment of the present invention.

According to the present invention in its preferred embodiment, the essential elements of the system are depicted in the perspective view of FIG. 1. A sample stage 1 has a hard steel wedge 2 placed on it which acts as a stress inducing element. Two slots 8 in sample stage 1 allow the two arms 3 of a clamp 4 to slide through the sample stage 1. A sample 7 is held by the two arms 3 of the clamp 4 and pulled against the wedge 2. A micrometer 5 including a gear 6 mounted to threaded rod 5a, is threaded through the lower part of the clamp 4, pulling the clamp 4 away from the stage 1 as threaded rod 5a pushes against stage 1.

Figure 2:
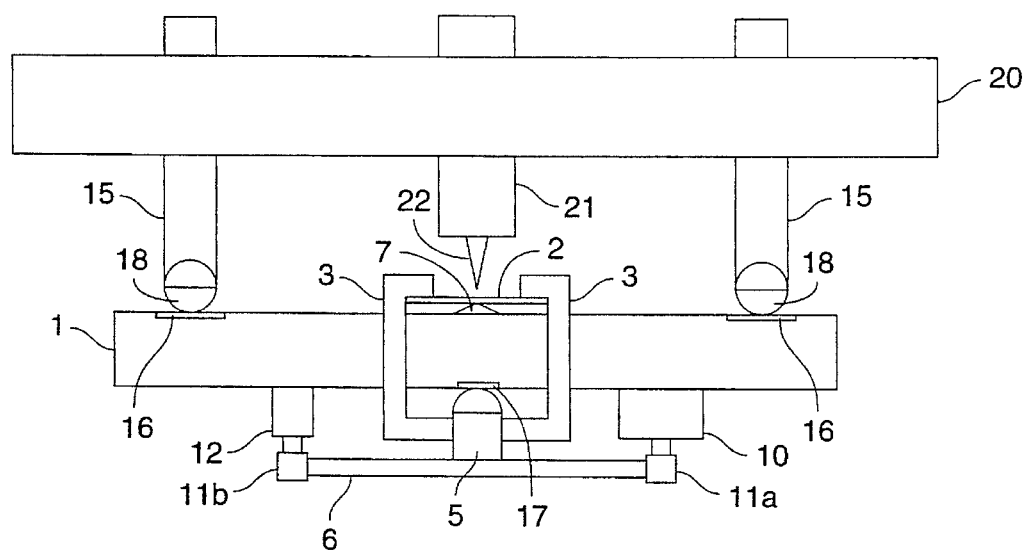
FIG. 2 is a cross-sectional view of the stress cell of FIG. 1 showing it mounted to a scanning probe microscope that scans the sample from above.

As depicted in FIG. 2, the stage 1 may be mounted onto a scanning probe microscope that scans and approaches the sample from above. Such a microscope is described in co-pending U.S. patent application Ser. No. 08/388,068 which is hereby incorporated by reference herein as if set forth fully herein. This microscope has three plungers 15 (two at the front as shown and one in the back which is not shown here) which have magnetic balls 18 at their ends and act to suspend the sample stage 1 from the scanning probe microscope. According to a presently preferred embodiment, magnetic balls 18 fasten onto three magnetic disks 16 which are embedded in the sample stage 1. This arrangement provides additional holding force over magnets against a pure steel plate. Alternatively, the sample stage may be incorporated into a support housing the stress cell and related equipment and the microscope may rest on that support. The three plungers 15 are adjusted so that the scanning probe 22 is lowered into the proximity of the sample surface for imaging. The surface topographical features are mapped as the scanning probe 22 is scanned over the surface by the piezoelectric scanner 21. A motor 10 is preferably mounted underneath the stage. It has a gear 11a mounted at the end of its drive-shaft which couples to the larger gear 6 on the micrometer 5. According to a presently preferred embodiment, a gear reduction ratio of 1:80 is used. A rotation counter 12 is also mounted underneath the stage, and it is coupled to the gear 6 on the micrometer 5 with a small gear 11b. A force sensor 17 is mounted on the bottom of the stage at the point where the apex of the micrometer 5 contacts the stage. It is used to calculate the shear modulus of the sample since the bending moment may be calculated precisely from the measured force and the geometry of the clamp as well known to those of ordinary skill in the art.

Figure 3:
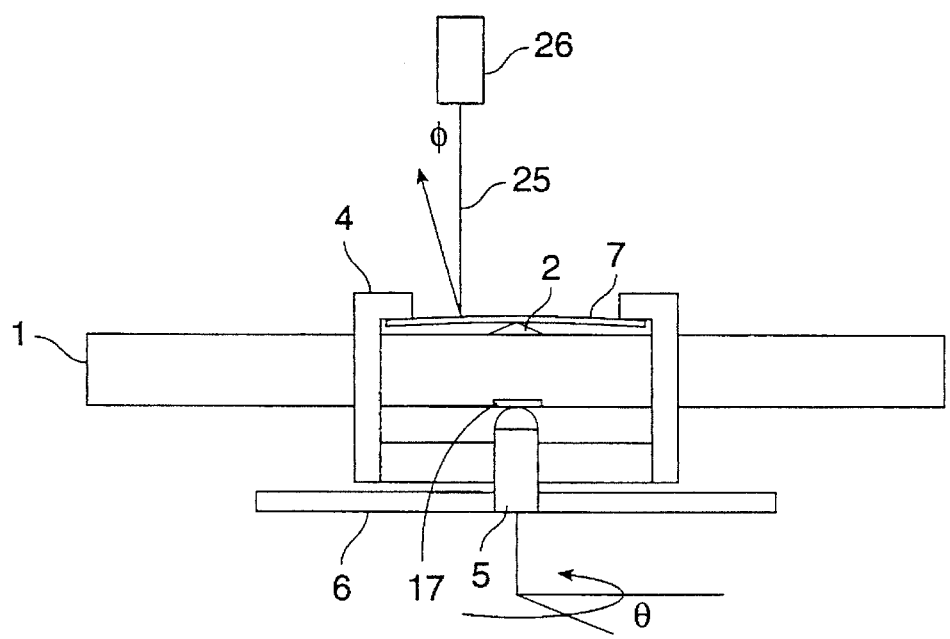
FIG. 3 is a cross-sectional view of a stress cell according to the present invention during a calibration procedure.

FIG. 3 shows a preferred method for calibrating the bending motion. An optical beam 25 from a laser diode 26 is reflected by the bent sample surface. The reflection angle φ is twice the bending angle of the sample. This angle is determined by direct measurement of the changes of the reflection angle as the sample is bent. It is calibrated against the rotation angle θ of the micrometer 5.

Figure 4:
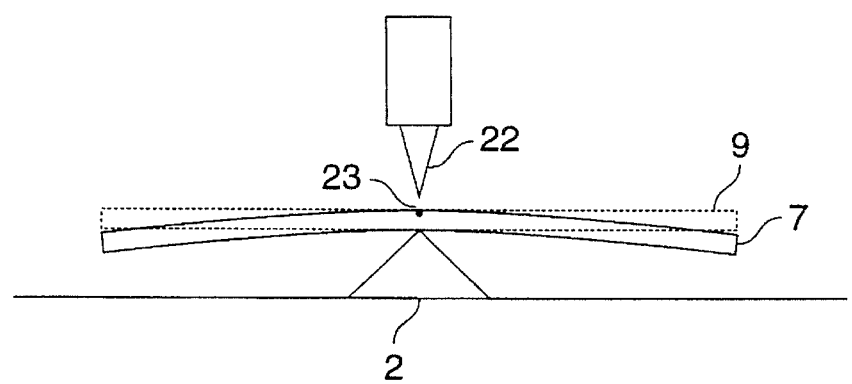
FIG. 4 is a cross-sectional view of a stressed sample undergoing scanning probe microscopy.

As depicted in FIG. 4, the point on the sample surface above the wedge 23 is kept at the same height before 9 and after 7 a bending moment is generated. This is essential for in situ imaging using a scanning probe microscope.

Thus, the system described in the present invention is easily set up without costly equipment and need for a high degree of training, yet it provides atomic-scale information, the highest resolution obtained to date, on surface structural changes under an applied stress.

While illustrative embodiments and applications of this invention have been shown and described, it would be apparent to those skilled in the art that many more modifications than have been mentioned above are possible without departing from the inventive concepts set forth herein. In particular, it is expected that many other shapes could be substituted for triangular-shaped wedge 2 and that other materials could be substituted for its hard steel. The invention, therefore, is not to be limited except in the spirit of the appended claims.

What is claimed is:

1. A stress cell for holding and applying stress to a sample surface to be scanned by a scanning probe microscope, said stress cell comprising:

a sample stage having an upper and a lower surface and including at least two apertures connecting said upper and lower surface;

a stress inducing unit fixedly mounted with respect to said upper surface of said stage;

a clamp for holding a sample surface over and in contact with said stress inducing unit, said clamp including at least two arms, each of said arms having a first end and a second end, and each of said arms extending through one of said apertures, said first ends of said arms of said clamp adapted to receive and hold the sample surface;

a micrometer including a threaded plate and a threaded rod, said second ends of said arms of said clamp fixedly attached to said threaded plate, said threaded rod adapted to engage said lower surface of said stage and thereby pull the sample surface into contact with said stress inducing unit.

2. A stress cell according to claim 1 further comprising a gear attached to said threaded rod.

3. A stress cell according to claim 2 further comprising a motor coupled to said gear.

4. A stress cell according to claim 2 further comprising a turns counter coupled to said gear.

5. A stress cell according to claim 1 wherein said stress inducing unit is a steel wedge of triangular cross-section.

6. A stress cell according to claim 1 further comprising a force sensor located in said sample stage directly beneath said stress inducing unit.

7. A stress cell for holding and applying stress to a sample surface to be scanned by a scanning probe microscope, said stress cell comprising:

a sample stage having an upper and a lower surface and including at least two apertures connecting said upper and lower surface;

a stress inducing unit fixedly mounted with respect to said upper surface of said stage;

a clamp for holding a sample surface over and in contact with said stress inducing unit, said clamp including at least two arms, each of said arms having a first end and a second end, and each of said arms extending through one of said apertures, said first ends of said arms of said clamp adapted to receive and hold the sample surface;

a block, said second ends of said arms of said clamp fixedly attached to said block;

means for urging said block away from said sample stage and thereby pull the sample surface into contact with said stress inducing unit.

8. A stress cell according to claim 7 wherein said stress inducing unit is a steel wedge of triangular cross-section.

9. A stress cell according to claim 7 further comprising a force sensor located in said sample stage directly beneath said stress inducing unit.

\* \* \* \* \*

UNITED STATES PATENT AND TRADEMARK OFFICE
CERTIFICATE OF CORRECTION

PATENT NO. : 5,500,535
DATED      : March 19, 1996
INVENTOR(S) : Tianwei Jing

It is certified that error appears in the above-indentified patent and that said Letters Patent is hereby corrected as shown below:

In the Drawings:

In FIG. 2, replace the numeral "7" with --2--.

In FIG. 2, replace the numeral "2" with --7--.

Signed and Sealed this

Twenty-second Day of October, 1996

*Attest:*

BRUCE LEHMAN

*Attesting Officer*     *Commissioner of Patents and Trademarks*